(12) United States Patent
Elton

(10) Patent No.: US 10,806,907 B2
(45) Date of Patent: Oct. 20, 2020

(54) BALLOON WITH RADIOPAQUE ADHESIVE

(75) Inventor: Richard K. Elton, Queensbury, NY (US)

(73) Assignee: C.R. BARD, INC., Tempe, AZ (US)

( * ) Notice: Subject to any disclaimer, the term of this patent is extended or adjusted under 35 U.S.C. 154(b) by 2352 days.

(21) Appl. No.: 13/062,131

(22) PCT Filed: Sep. 2, 2009

(86) PCT No.: PCT/US2009/055663
§ 371 (c)(1),
(2), (4) Date: Mar. 3, 2011

(87) PCT Pub. No.: WO2010/027998
PCT Pub. Date: Mar. 11, 2010

(65) Prior Publication Data
US 2011/0160661 A1 Jun. 30, 2011

Related U.S. Application Data

(60) Provisional application No. 61/094,696, filed on Sep. 5, 2008.

(51) Int. Cl.
*A61M 25/10* (2013.01)
*A61F 2/958* (2013.01)

(52) U.S. Cl.
CPC .......... *A61M 25/10* (2013.01); *A61M 25/104* (2013.01); *A61F 2/958* (2013.01); *A61F 2002/9583* (2013.01); *A61M 2025/1004* (2013.01); *A61M 2025/1075* (2013.01); *A61M 2025/1079* (2013.01)

(58) Field of Classification Search
CPC ............ A61F 2002/9583; A61F 2/958; A61M 2025/1075; A61M 2025/1079; A61M 25/10; A61M 25/104; A61M 2205/32; A61B 17/12022; A61B 17/12109; A61B 17/12136
USPC .................. 604/103.06, 96.01, 48, 19, 93.01
See application file for complete search history.

(56) References Cited

U.S. PATENT DOCUMENTS

| 3,755,525 A | 8/1973 | Sheridan et al. |
| 4,364,392 A | 12/1982 | Strother et al. |
| 4,413,989 A | 11/1983 | Schjeldahl et al. |
| 4,702,252 A * | 10/1987 | Brooks ............. A61M 25/0108 604/103 |

(Continued)

FOREIGN PATENT DOCUMENTS

| EP | 0553960 A1 | 8/1993 |
| EP | 0 775 500 A1 | 5/1997 |

(Continued)

*Primary Examiner* — Rebecca E Eisenberg
*Assistant Examiner* — Weng Lee
(74) *Attorney, Agent, or Firm* — King & Schickli, PLLC

(57) ABSTRACT

A radiopaque balloon with a composite wall having a radiopaque adhesive affixing inner and outer layers of the balloon. The radiopaque adhesive provides a radiographic image of the balloon wall with or without the use of a radiopaque contrast media to inflate the balloon. A radiographically fainter image is provided as the balloon is inflated with well-defined edges of a balloon image, and the total radiopacity of the balloon does not change as the balloon is inflated. Also, a method of imaging a balloon wall and a method of imaging a radiopaque adhesive between two layers of a balloon wall are provided.

12 Claims, 7 Drawing Sheets

(56) References Cited

U.S. PATENT DOCUMENTS

| | | | |
|---|---|---|---|
| 4,946,464 A | 8/1990 | Pevsner | |
| 5,112,304 A | 5/1992 | Barlow et al. | |
| 5,171,232 A | 12/1992 | Castillo et al. | |
| 5,261,878 A | 11/1993 | Galindo | |
| 5,669,879 A | 9/1997 | Duer | |
| 5,713,860 A | 2/1998 | Kaplan et al. | |
| 5,713,913 A | 2/1998 | Lary et al. | |
| 5,752,522 A | 5/1998 | Murphy | |
| 5,759,174 A | 6/1998 | Fischell et al. | |
| 5,792,172 A * | 8/1998 | Fischell | A61F 2/958 606/194 |
| 5,797,877 A * | 8/1998 | Hamilton | A61L 29/049 604/264 |
| 5,807,327 A * | 9/1998 | Green | A61F 2/958 604/194 |
| 5,858,556 A * | 1/1999 | Eckert | A61F 2/82 148/521 |
| 5,873,811 A | 2/1999 | Wang et al. | |
| 5,891,114 A | 4/1999 | Chien et al. | |
| 6,488,653 B1 | 12/2002 | Lombardo | |
| 6,501,992 B1 | 12/2002 | Belden et al. | |
| 6,547,804 B2 | 4/2003 | Porter et al. | |
| 6,599,448 B1 * | 7/2003 | Ehrhard, Jr. | A61K 49/0442 252/408.1 |
| 6,652,507 B2 | 11/2003 | Pepin | |
| 6,652,568 B1 * | 11/2003 | Becker | A61F 2/958 604/103.1 |
| 6,673,025 B1 | 1/2004 | Richardson et al. | |
| 6,761,708 B1 * | 7/2004 | Chiu | A61M 25/0009 604/103.1 |
| 6,884,234 B2 | 4/2005 | Aita et al. | |
| 7,008,979 B2 | 3/2006 | Schottman et al. | |
| 7,195,612 B2 | 3/2007 | van Sloten et al. | |
| 2001/0044624 A1 * | 11/2001 | Seraj | A61M 25/0138 606/41 |
| 2002/0198559 A1 | 12/2002 | Mistry et al. | |
| 2003/0036728 A1 | 2/2003 | Samson et al. | |
| 2003/0083579 A1 * | 5/2003 | Aita | A61F 2/958 600/470 |
| 2004/0078052 A1 | 4/2004 | St. Pierre et al. | |
| 2004/0122509 A1 | 6/2004 | Brodeur | |
| 2006/0058867 A1 * | 3/2006 | Thistle | A61L 27/427 623/1.13 |
| 2006/0085022 A1 * | 4/2006 | Hayes | A61M 25/104 606/192 |
| 2007/0010844 A1 * | 1/2007 | Gong | A61B 17/8855 606/192 |
| 2007/0010845 A1 | 1/2007 | Gong et al. | |
| 2007/0093865 A1 | 4/2007 | Beckham | |
| 2007/0100280 A1 | 5/2007 | van Sloten et al. | |
| 2007/0244501 A1 | 10/2007 | Horn et al. | |
| 2008/0086082 A1 * | 4/2008 | Brooks | A61M 25/10 604/100.03 |
| 2008/0243069 A1 | 10/2008 | Krivoruchko | |
| 2009/0299327 A1 | 12/2009 | Tilson et al. | |
| 2010/0158193 A1 | 6/2010 | Bates | |
| 2010/0234875 A1 | 9/2010 | Allex et al. | |
| 2010/0262182 A1 * | 10/2010 | Moszner | A61B 17/0057 606/213 |
| 2011/0009818 A1 | 1/2011 | Goff | |
| 2011/0198019 A1 | 8/2011 | Tilson | |

FOREIGN PATENT DOCUMENTS

| | | |
|---|---|---|
| EP | 0 807 446 | 11/1997 |
| JP | H01-305965 A | 12/1989 |
| JP | H02-51556 A | 2/1990 |
| JP | H03-277374 A | 12/1991 |
| JP | H05-76598 A | 3/1993 |
| JP | H09-327515 A | 12/1997 |
| JP | 2001521491 A | 11/2001 |
| JP | 2004-536672 A | 12/2004 |
| JP | 2006-503642 A | 2/2006 |
| WO | WO8404462 | 11/1984 |
| WO | 03037421 A2 | 5/2003 |

* cited by examiner

BALLOON WITH RADIOPAQUE ADHESIVE

This application is the national stage of PCT/US2009/55663, and claims the benefit of U.S. Provisional Patent Application Ser. No. 61/094,969, Sep. 5, 2008 the disclosure of which is incorporated herein by reference.

TECHNICAL FIELD

The subject invention relates to balloons having a radiopaque adhesive and, more particularly, to layered non-compliant medical balloons with a radiopaque adhesive between balloon layers.

BACKGROUND ART

Existing balloons that are imaged with an imaging system are believed to provide a faint image due to the minimal ability of the balloon wall to absorb or reflect imaging radiation. Such balloons are also believed to provide an image that is not significantly distinguishable from surrounding structures and tissues, and to provide an image that does not readily indicate the inflation status of the balloon or the position of the balloon wall without the use of an imaging fluid. Accordingly, the location and inflation status of such balloons are enhanced by inflating the balloon with a fluid containing a material that provides a more pronounced image. A shortcoming of such inflation-dependent imaging methods is that the image obtained is of the fluid within the balloon and not of the balloon itself. It is also believed that imaging fluids that provide an adequate image also possess a viscosity that undesirably increases the time required to inflate and deflate the balloon when the fluid is delivered to the balloon through a narrow lumen. Another shortcoming is that such imaging fluids are more expensive and require more preparation time as compared to less viscous and pre-made fluids such as physiological saline.

In conventional radiography, when a balloon is inflated with an inflation fluid containing an imaging fluid such as contrast media, the contrast media presents the strongest image at the center portion of the imaged balloon and the weakest image at the edges of the radiographic image. This is because the x-rays traveling through the center of the balloon pass through a greater quantity of contrast media than at the peripheral edges of the balloon image. This difference results in an image of the fluid in the balloon that has a strongly-imaged center and undesirably faint edges of the image, that is believed to provide an undefined or unclear image of the peripheral edge of the balloon, thus making it difficult to determine the exact edge of the balloon, reducing the precision of the placement of the inflated balloon, and making it difficult to determine whether the balloon has encountered any constrictions in the vessel being dilated.

It is thus desirable to provide a balloon that does not require inflation with an imaging fluid, and to provide a balloon that permits direct imaging of the balloon with or without the use of an imaging fluid.

DISCLOSURE OF THE INVENTION

A balloon and catheter are provided that includes a balloon wall with inner and outer layers with a radiopaque adhesive disposed between and affixing the inner and outer layers. The radiopaque adhesive includes an adhesive base and a radiopaque material dispersed in the adhesive base. Alternatively, the adhesive base itself is composed of an intrinsically radiopaque polymeric material with or without another radiopaque material dispersed in the adhesive base. The balloon preferably also includes layers of fibers that reinforce the balloon, and the fibers are preferably disposed between the inner and outer layers of the balloon wall within or between layers of the radiopaque adhesive. In an alternative embodiment, the fibers are arranged in a pattern on the balloon, as layers formed over each other as a weave or braid within a fiber layer, or woven or braided together to form a single fiber layer. In another embodiment, the radiopaque adhesive is disposed within the balloon wall to form a pattern.

The balloon is preferably a compliant balloon or, more preferably, a semi-compliant balloon. Compliant balloons allow for the doubling of the outer diameter of the balloon when inflated from an operating pressure to a rated burst pressure, and are made of latex, for example. Semi-compliant balloons provide for an increase in the balloon outer diameter by 10-15%, and are made of Nylon, for example. The balloon is most preferably a non-compliant balloon that inflates to a predetermined size and shape with a predetermined surface area, circumference, or length. The preferred non-compliant balloon preferably provides for an increase in an inflated outer diameter that is within 5% of a nominal balloon diameter. The balloon is also preferably a high-pressure balloon having a rated burst pressure of 20 atm or greater, for example. Alternatively, the balloon is a low-pressure balloon having a rated burst pressure of less than 6 atm.

The balloon preferably has a predetermined total radiographic quantity that is the total amount of radiopaque material present in the structure of the entire balloon, which includes the radiopaque material present in the adhesive of the balloon wall and does not include radiopaque material that is temporarily added to the balloon such as for inflation. When using a non-radiopaque inflation fluid, the balloon as a whole contains the same amount of radiopaque material regardless of inflation state as the total quantity of the radiopaque material within the balloon wall remains constant. The balloon preferably also possesses a radiographic density that is a ratio of the total radiographic quantity relative to the volume of the balloon, and which is subject to change as the balloon increases or decrease volume between the uninflated and inflated states of the balloon as the total quantity of the radiopaque material in the balloon remains constant while the balloon volume changes. The balloon also preferably provides a total radiographic image intensity that characterizes the image that the entire balloon presents to an imaging device when viewed, and that becomes less intense as the balloon is inflated and the fixed quantity of radiopaque material in the balloon is dispersed over a greater volume. The radiographic image intensity can also characterize the image present at only a portion of the balloon, such as at the center of the balloon image presented by an imaging system viewing the balloon from a side of the balloon.

Also provided is a fiber-reinforced balloon with a wall that includes a radiopaque adhesive that does not add to the radial thickness of the wall. The fibers of the fiber-reinforced balloon are preferably disposed in layers with one fiber layer over and contacting an adjacent fiber layer. Preferably, the radiopaque adhesive is disposed in spaces between adjacent fibers of the fiber layers to affix one fiber layer to an adjacent fiber layer.

Also provided is a method of imaging a balloon wall, and a method of imaging a radiopaque adhesive between two layers of a balloon wall. A preferred method of making a balloon wall with a radiopaque adhesive is provided that includes applying a radiopaque adhesive between two layers of a balloon wall. Also provided is a method of treating a region of a human body by imaging a wall of a balloon, and a method of imaging a radiopaque adhesive disposed between two layers of a balloon wall.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

MODE(S) FOR CARRYING OUT THE INVENTION

The description provided below and in regard to the figures applies to all embodiments unless noted otherwise, and features common to each embodiment are similarly shown and numbered.

Figure 1:
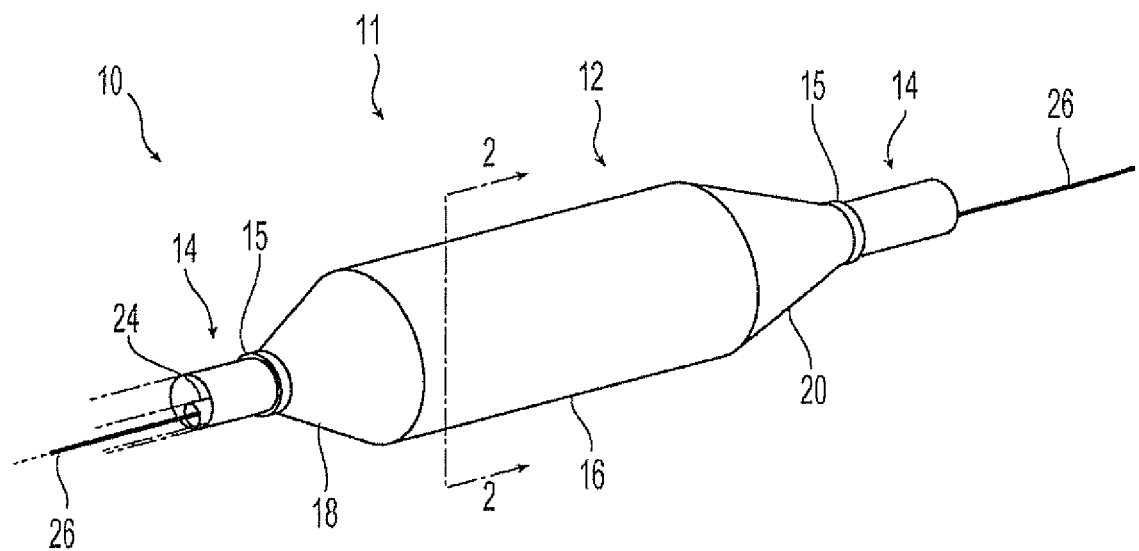
FIG. 1 is an isometric view of a portion of an exemplary catheter and of an exemplary balloon.
Figure 2:
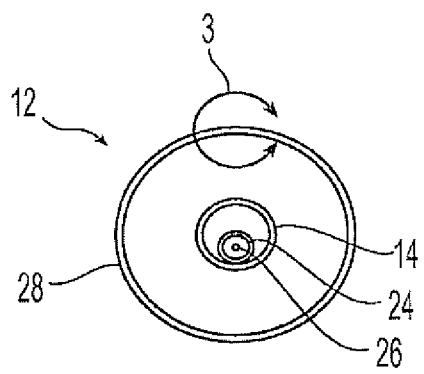
FIG. 2 is a cross-sectional view of the catheter and balloon of FIG. 1.

Provided is a catheter 10 having a distal portion 11 with a balloon 12 mounted on a catheter tube 14. Referring to FIGS. 1 and 2, the balloon 12 has a central section 16 and conical end sections 18, 20 that reduce in diameter to join the central section 16 to the catheter tube 14. The balloon 12 is sealed to catheter tube 14 at balloon ends 15 on the conical end sections 18, 20 to allow the inflation of the balloon 12 via one of more lumens extending within catheter tube 14 and communicating with the interior of the balloon. The catheter tube 14 also includes a guidewire lumen 24 that directs the passage of the guidewire 26 through the catheter 10. Balloon 12 has a multi-layered balloon wall 28 forming the balloon 12, and preferably is a non-compliant balloon that has a balloon wall 28 that maintains its size and shape in one or more directions when the balloon is inflated. The balloon 12 preferably has a pre-determined surface area that remains constant during and after inflation, and also preferably has a pre-determined length and pre-determined circumference that each, or together, remain constant during and after inflation. The balloon 12 also preferably unfolds to a pre-determined diameter when inflated. Balloon 12 is also preferably non-compliant in that it maintains a pre-determined shape when inflated.

Figure 3:
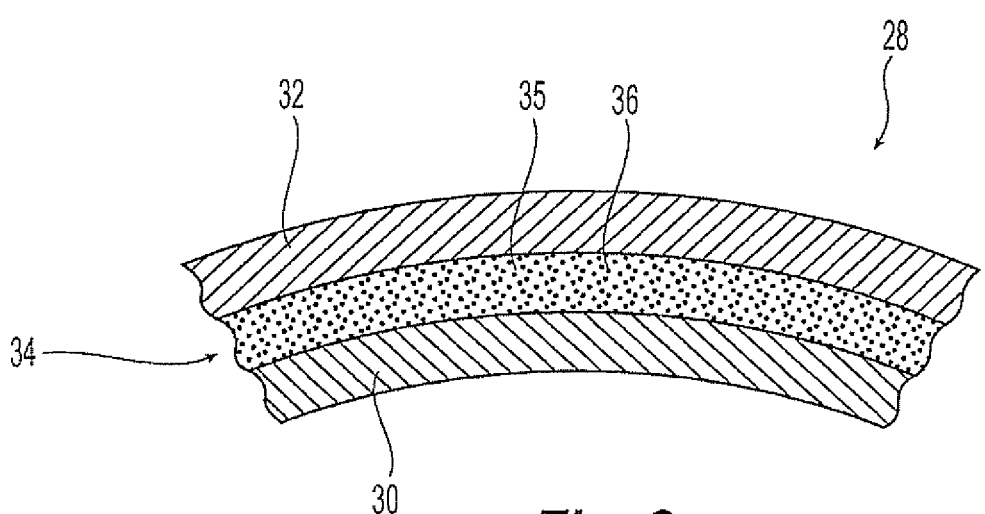
FIG. 3 is a cross-sectional view of a portion of the balloon of FIG. 1, and an enlarged view of a portion of the balloon of FIG. 2.

The balloon wall 28 includes an inner layer 30 and an outer layer 32. Between layers 30, 32 is an adhesive 34 that secures the outer layer 32 to the inner layer 30. FIG. 3 illustrates an exemplary arrangement of layers 30, 32 and adhesive 34. The adhesive 34 preferably includes an adhesive base 35 and a radiopaque material 36 dispersed within the adhesive base 35. The adhesive base 35 is preferably a laminating adhesive such as a: thermoplastic polyurethane, thermoplastic acrylic, rubber-based adhesive, polyamide, polyvinyl acetate, polyethylene-vinyl alcohol copolymer, solvent-borne adhesive, hot-melt adhesive, polyvinyl butyral, cellulosic derivatives such as cellulose-acetate-butyrate, silicone RTV, or other similar flexible adhesives capable of laminating films or bonding plastic materials together. More preferably, the adhesive base 35 is a solvent-borne adhesive of a flexible thermoplastic material, such as a polyurethane, polyamide, or acrylic polymer. Most preferably, the adhesive base 35 is a thermoplastic polyurethane adhesive that is applied as a solution, and re-activated with a solvent such as a methyl ethyl ketone applied to the dried adhesive base 35. The placement of the adhesive 34 between the inner and outer layers 30 and 32 preferably provides a barrier between the adhesive and the internal or external environments of the balloon 12, so as to seal and isolate the adhesive 34 from the patient and limit the patient's contact with the adhesive.

In an alternative, the adhesive base 35 itself is composed of an intrinsically radiopaque polymeric material that contains higher atomic weight heteroatoms covalently or ionically bound into the polymer structure, and that imparts radiopacity to the polymer itself. Such polymers include polymers that have covalently bonded iodine or bromine in the polymer structure. Such polymers also include polymers with ionically bonded metals such as cerium, gadolinium, or other rare earth metals, or barium, bismuth, or other metals that have good radiopacity. Another intrinsically radiopaque polymer includes a polymer that is capable of complexing a radiopaque compound in the molecular structure of the polymer, such as a polymer that contains functional groups that bind with and form complexes with radiopaque compounds such as iodine, bismuth compounds, rare earth salts, or other substances that exhibit good radiopacity. Yet another embodiment includes an adhesive that is composed of an intrinsically radiopaque polymer, such as the polymers described above, to which the radiopaque material 36 is added and dispersed throughout the adhesive base 35.

Alternatively, the adhesive base 35 is a two-part adhesive in which the two components are applied separately or as a pre-made mixture to the inner or outer layers 30, 32 that interact to form the adhesive base. Examples of two-part adhesives include crosslinked polyurethanes, thermoset acrylic adhesives, epoxies, crosslinked polyureas, polyurethaneureas, two-part silicone rubber adhesives, and other two-component adhesive materials. In yet another alternative, the adhesive base is the reaction product of a first and second substance, with the first substance being a component of the inner or outer layers 30, 32, and the second substance being applied to the layers 30, 32 to interact with the first substance to form a two-part adhesive, or to activate the first substance to form the adhesive. In still another alternative, the adhesive base is a substance that is activated by an external factor to cause the adhesive base to alter and form the adhesive by the application of heat, pressure, or radiation. Examples of externally-activated adhesives include polyamide hot melt adhesives, ethylene vinyl acetate copolymers, thermoplastic polyurethanes, hot-melt adhesives used in lamination, and pressure sensitive adhesives such as acrylic, silicone, and rubber-based pressure sensitive adhesives.

The radiopaque material 36 is distributed in the adhesive base 35 in a sufficient quantity to permit imaging of the balloon wall 28 by an imaging method. The radiopaque material 36 is preferably a material that absorbs or reflects significant quantities of x-ray or other diagnostically-significant radiation to render an image during a imaging procedure. The radiopaque material 36 is more preferably a material that absorbs x-rays. Examples of radiopaque materials include dense metals such as tungsten, tantalum, silver, tin, platinum, gold, iridium, and similar metals known to absorb x-rays. Other examples of radiopaque materials include inorganic compounds that absorb x-rays. Further examples of radiopaque materials include barium sulfate, bismuth trioxide, bismuth subcarbonate, bismuth oxychloride, cerium oxide, compounds of tungsten, tantalum, and rare earth metals. Most preferably, the radiopaque material 36 is tungsten. The radiopaque material 36 is preferably evenly distributed in the adhesive 34. Alternatively, the radiopaque materials are distributed in the adhesive to form patterns, or to facilitate a darker or lighter image at different locations in the balloon wall 28 to form a pattern in the resulting image or to compensate for areas of the balloon that provide a darker or lighter image resulting from the changes in the geometry or structure of the balloon or changes in balloon wall thickness, such as at the conical end sections 18, 20 where the diameter of the balloon changes.

The adhesive 34 is preferably a predetermined mixture of the adhesive base 35 and the radiopaque material 36 distributed within the adhesive base. The volume of radiopaque material distributed in the adhesive is preferably used to determine the intensity of the image that results during x-ray imaging. Preferably, the adhesive is composed of 40-98 volume-% adhesive base and 2-60 volume-% radiopaque material. More preferably, the adhesive is composed of 55-80 volume-% adhesive base and 20-45 volume-% radiopaque material. Most preferably, the adhesive is composed of 65 volume-% adhesive base and 35 volume-% radiopaque material.

The adhesive 34 is preferably placed along the entire length and circumference of balloon wall 28 to bond the entire mating surfaces of the inner and outer layers 30, 32 to each other. Alternatively, the adhesive 34 is disposed at only portions of the wall and another adhesive, without the radiopaque material 36, is disposed along the remainder of the balloon wall 28 to form a pattern in the radiopaque image of the balloon 12. In another alternative, the quantity of radiopaque material 36 in the adhesive 34 is varied to form a pattern in the image of the balloon 12 obtained with an imaging system. The patterns of these alternative embodiments preferably form an image of lines or bands in the balloon wall 28. In yet another alternative, the quantity of the radiopaque material in the adhesive is modified to provide a consistent image of the inflated or deflated balloon 12 with an imaging system, by controlling the placement of the radiopaque material 36 to compensate for or minimize variations or patterns created in the image of the balloon 12 caused by variations of balloon geometry or by the presence of a device carried on the balloon.

Figure 4A:
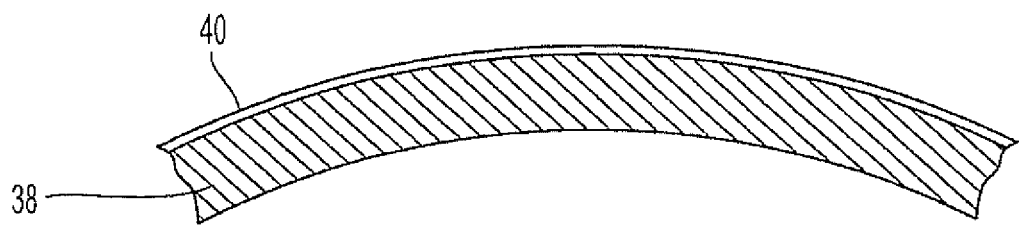
FIGS. 4A-4D are cross-sectional views illustrating the manufacture of another embodiment of a balloon.

The balloon wall 28 is preferably formed with successive layers. Referring to FIG. 3, the balloon is preferably formed by providing the inner layer 30, applying the adhesive 34, and providing the outer layer 32. The adhesive 34 is preferably applied onto the exterior of the inner layer 30 by spraying, dipping, brushing, or by other suitable means. Referring to FIG. 3, the adhesive 34 is preferably a single layer that is subsequently covered by the outer layer 32 to form the balloon wall 28. In an another embodiment, reinforcing fibers or filaments are added between the inner and outer layers 30, 32 to increase the balloon strength under pressure or to control the compliance and shape of the finished balloon In a preferred embodiment, the balloon wall is formed with successive layers disposed on a base balloon. Referring to FIG. 4A, a base balloon 38 is provided as an initial balloon structure in the manufacture of the balloon. The base balloon is preferably composed of any thermoplastic or thermoset material that is capable of being formed into the desired balloon shape. Examples of base balloon materials include polyamides, polyesters, polyurethanes, polyethylene, polypropylene, polyamide-polyether block copolymers, polyimides, crosslinked polyethylene, ionomers such as Surlyn®, crosslinked polyurethanes, and other similar polymers that possess the desired properties of strength, flexibility, and distensibility for use in a compliant or non-compliant balloon. The base balloon 38 is preferably a PET tube that is stretched under heat and pressure into the desired balloon form, such as to form a cylinder having the central section 16, conical end sections 18, 20, and balloon ends 15 as illustrated in FIG. 1.

After formation of the base balloon 38, adhesive is applied to the exterior surface of the base balloon 38 as a first adhesive layer 40. The first adhesive layer 40 is preferably applied onto the exterior of the base balloon 38 by spraying, dipping, brushing, or by other suitable means. Preferably, although not shown in FIG. 4A, the first adhesive layer 40 includes a radiopaque material distributed within the adhesive. In an alternative embodiment, the first adhesive layer 40 does not include a radiopaque material.

Figure 4B:
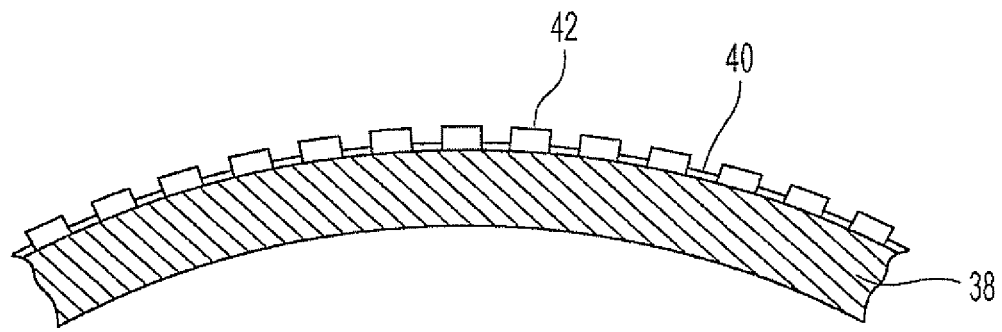

Referring to FIG. 4B, a series of first fibers 42 are applied to the base balloon 38 to form a fiber layer, and affixed to the base balloon 38 by the first adhesive layer 40. Preferably, some of the adhesive of first adhesive layer 40 moves to partly fill the spaces formed between adjacent fibers 42, with only a minimal or negligible amount of adhesive remaining directly between the fibers 42 and the outer surface of base balloon 38. The movement of the adhesive to the spaces between adjacent fibers 42 keeps the adhesive from contributing to the wall thickness of the balloon wall while still providing the desired adhesion properties to affix the first fibers 42 to the base balloon 38. The first fibers 42 are preferably disposed in the direction of the longitudinal axis of the balloon or catheter. More preferably, the first fibers 42 extend along the exterior surface of the balloon base 38 for different or varying lengths. Most preferably, some of the fibers of first fibers 42 extend along the length of the only the central section 16 of the balloon, and some of the first fibers 42 extend along the entire length of the balloon to cover the central section 16 and the conical end sections 18, 20. The use of varying fibers lengths for the first fibers 42 provides for fewer fibers at the conical end sections 18, 20, which prevents the fiber layer formed by the first fibers 42 from bunching up or creasing as the diameter of the balloon reduces along the length of the conical end sections 18, 20.

Any high strength fibers or filaments are preferably used to impart the desired properties to the balloon. Examples of suitable fibers include ultrahigh molecular weight polyethylene such as Spectra® or Dyneema® fibers, polyamide fibers, polyimide fibers, ultrahigh molecular weight polyurethane fibers such as Technora®, fibers made from polyesters or polypropylene, or finely drawn strands of metals such as stainless or high tensile steel. The first fibers 42 are preferably ultra-high molecular weight polyethylene or Technora® fibers having a filament diameter of about 12 microns that has been flattened to a rectangular profile of about 0.0005 of an inch by 0.020 of an inch.

Figure 4C:
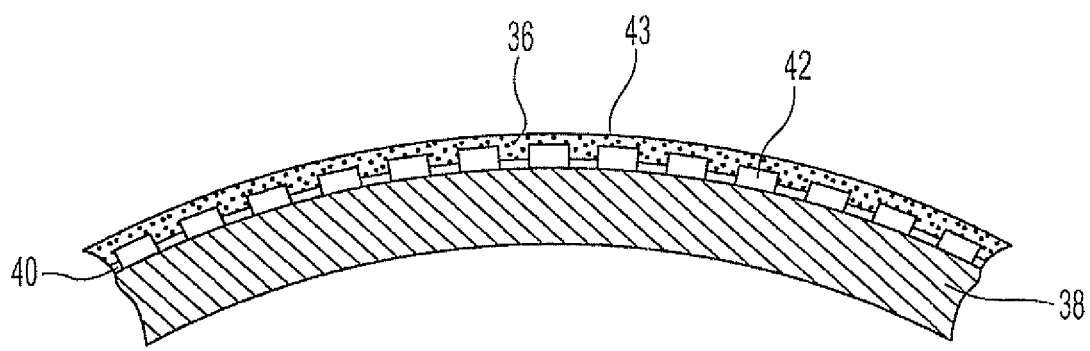

Referring to FIG. 4C, more adhesive is applied to the exterior of the composite formed by based balloon 38, first adhesive layer 40, and first fibers 42. Preferably, the adhesive 34 with the radiopaque material 36 is applied to the exterior of the first adhesive layer 40 and first fibers 42 to form an intermediate adhesive layer 43. The adhesive of the intermediate adhesive layer 43 is preferably applied as a spray, or deposited by dipping into a bath, or by brush or other suitable means. Applying by spray is more preferable. In an alternative, the intermediate layer 43 is applied to form a radiopaque pattern by controlling the placement of the adhesive 34 on the composite, or by the use of another adhesive that does not have a radiopaque property and that is disposed over the composite in a desired pattern.

Figure 4D:
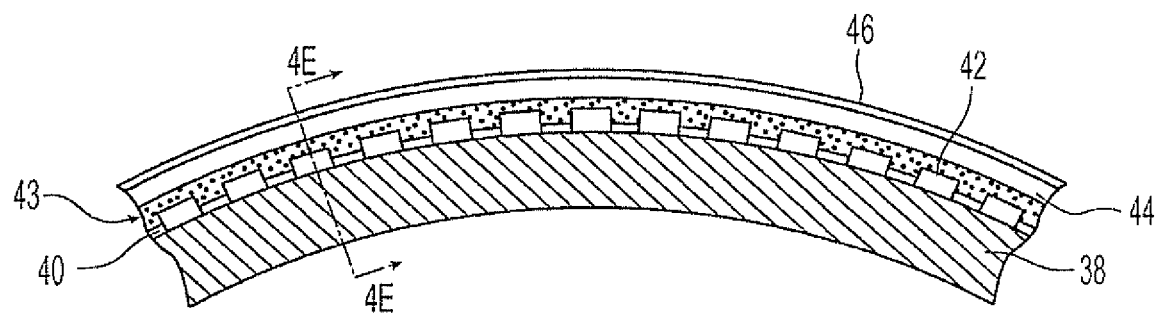
Figure 4E:
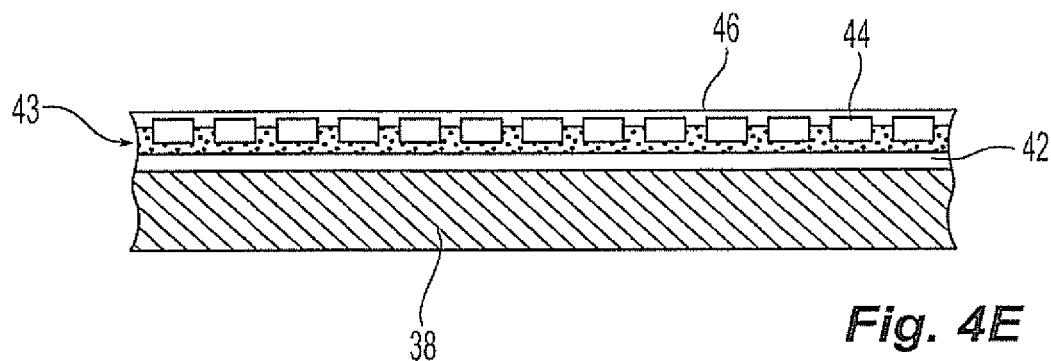
FIG. 4E is a cross-sectional view of the balloon wall of FIG. 4D.

Referring to FIG. 4D, a second fiber 44 is disposed over the intermediate adhesive layer 43 and affixed to the underlying first fibers 42 by the adhesive 34. The second fiber 44 is preferably composed of any of the aforementioned fiber materials and is more preferably a single ultra-high molecular weight polyethylene or Technora® fiber identical to the first fibers 42. The second fiber 44 is preferably wound circumferentially around the base balloon 38 to form a circumferential fiber layer helically extending along the longitudinal length of the balloon 12. Referring to FIGS. 4D-4E, a second adhesive layer 46, preferably identical to the first adhesive layer 40, is applied to the exterior of the composite of base balloon 38, layers 40 and 43, and fibers 42 and 44. The fibers are preferably disposed as layers with the layer of the second fiber 44 disposed over the layer of first fibers 42. Alternatively, the fibers form a weave or braided structure within a single layer, with the first fibers 42 disposed to form a first weave layer and the second fiber 44 disposed to form a weave with itself or with another fiber to form a second weave layer. In another alternative, the first fibers 42 and the second fiber 44 join together a weave or braided structure to form a single weave or braided layer.

Although not shown in FIGS. 4D-4E, the second adhesive layer 46 also preferably bonds to a protective outer film (not shown) of the balloon 12. It is preferable to include a protective outer film on the exterior surface of the balloon to provide abrasion resistance to the balloon surface and to protect the underlying fibers. Preferably, this film is an abrasion resistant material. Examples of abrasion resistant materials include polyesters, polyamide, polyamide-polyether block copolymers, polyurethanes, ionomers such as Surlyn®, polyethylene, polypropylene, and crosslinkable materials such as polyurethanes or polyethylene. Preferably, a polyether block copolymer such as Pebax® is used as the abrasion resistant material. In an alternative embodiment, the protective outer film is formed by melting and fusing the second adhesive layer 46 when heat is applied during manufacture. In another alternative, the protective outer film includes a radiopaque material dispersed within the film to impart additional radiopacity to the balloon.

In another alternative, a protective coating is applied to the balloon, instead of by bonding the radiopaque adhesive to a film or by forming a protective film from the adhesive itself Examples of protective coatings providing abrasion resistance include epoxies, polyurethanes, polyesters, alkyd resins, polyvinylbutyral, cellulose nitrate, polyvinyl acetate, phenolic resins such as phenol-formaldehyde resins, and amino resins such as amino-formaldehyde resins. The protective coating preferably includes some radiopaque material dispersed within it to impart additional radiopacity to the balloon.

In order to consolidate the laminated composite structure (of base balloon, fibers, adhesive layers, and protective outer film or coating) into a fused balloon wall, the composite is exposed to conditions that cause the layers to intimately bond together. Preferably, the composite of balloon 12 is heated in a die using heat and pressure to fuse the composite materials into a consolidated structure. Preferably, if the adhesive is a thermoplastic material, such as a thermoplastic polyurethane, the application of heat will also soften the adhesive and cause it to flow and bond to the composite materials of the balloon. Also preferably, if the adhesive contains a catalyst or is a two-part material that requires reaction of the two components in order to cure, the application of heat provides the means to accelerate the curing process.

Figure 4F:
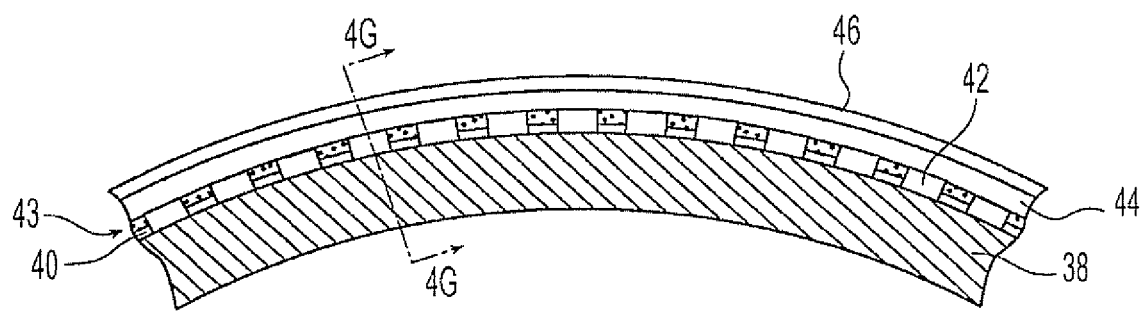
FIGS. 4F-4G are the same views presented in FIGS. 4D and 4E, respectively, but illustrating another exemplary embodiment.
Figure 4G:
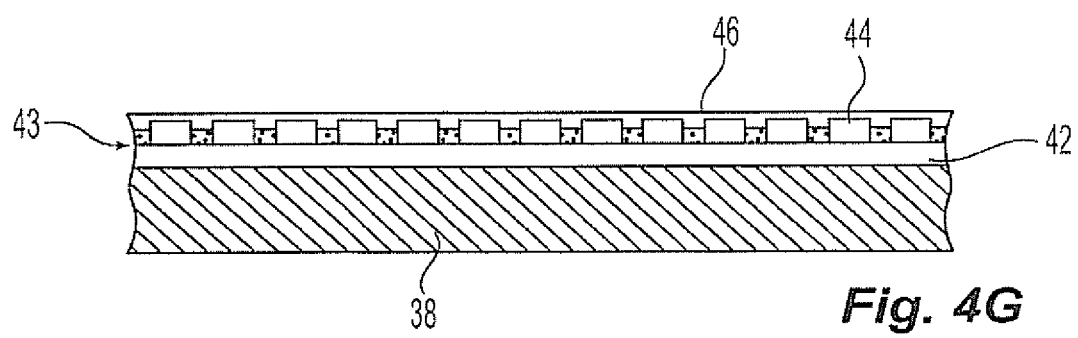

Each layer of adhesive is preferably applied in a single application. Alternatively, each layer of adhesive is applied as a composite of multiple applications to achieve a desired layer thickness or a desired disposition of radiopaque material. The adhesive 34 preferably has a radial thickness of 2-100 microns, more preferably has a radial thickness of 3-50 microns, and most preferably has a radial thickness of 10-40 microns. In a preferred embodiment having fiber reinforcement, the intermediate layer 43 has a thickness that allows radial contact between the first fibers 42 and second fiber 44 so as to cause the adhesive 34 of the intermediate layer 43 to move into and occupy the spaces between the adjacent first fibers 42 or adjacent windings of the second fiber 44, thereby allowing the intermediate layer 43 to be present in the balloon wall 28 but not add to the radial thickness of the balloon wall 28. FIGS. 4F and 4G illustrate an alternative embodiment to that shown in FIGS. 4D and 4E, respectively, in which the intermediate adhesive layer 43 is present but does not add to the radial thickness of the balloon wall 28. In an alternative, some of the adhesive layers, which have radiopaque or non-radiopaque properties, are comprised of materials that soften and flow during the lamination process.

Other embodiments of the radiopaque balloon are similarly constructed but without the reinforcing fibers. In this alternative embodiment, the balloon has a base balloon, a layer of radiopaque adhesive on the outside surface of the base balloon, and a final protective layer such as a film or coating over the exterior surface of the radiopaque adhesive. The radiopaque adhesive imparts radiopacity to the balloon and bonds the base balloon to the protective outer layer.

The adhesive 34 is alternatively applied in a pattern. The patterns are preferably made with the selective application of adhesive 34 when applying the intermediate adhesive layer 43, for example, with the use of a narrow PTFE tape that is wrapped over the first fibers 42 to mask areas of the balloon composite prior to the application of the intermediate adhesive layer 43. The PTFE tape is then removed after the application of the intermediate adhesive layer 43 to expose areas that do not have the adhesive 34. A layer of a non-radiopaque adhesive is then applied that does not have the radiopaque material 36 to coat the entire balloon composite, thereby placing an additional non-radiopaque adhesive layer over the first fibers 42 and the intermediate adhesive layer 43 and to fill in areas that were covered by the PTFE tape.

Alternatively, the manufacturing process illustrated in FIGS. 4A-4E and FIGS. 4F-4G is accomplished with the use of a mold or mandrel in place of the base balloon 38. The mold or mandrel is subsequently removed after the lamination of the balloon 12 to leave a balloon wall that does not have the base balloon 38, leaving the first adhesive layer 40 and first fibers 42 to form the interior surface of the balloon 12.

In another alternative, the balloon 12 includes a layer of marker material, such as a marker strip, marker filaments, or marker ring, preferably between the first fibers 42 and second fiber 44 at predetermined locations such as at the balloon ends 15 to form radiopaque markers identifying specific locations on the balloon 12. The radiopaque markers preferably have a different radiopacity than the radiopacity of the remainder of the balloon wall 28. The marker strips, filaments, or rings are preferably made from a material that exhibits the preferred properties of radiopacity, flexibility, malleability, and processability. Suitable materials for use as a marker include tantalum, tin, silver, gold, platinum, rhenium, iridium, palladium, hafnium, tungsten, lanthanum, and other metals that absorb x-rays. Preferable materials include silver and tin.

Figure 5A:
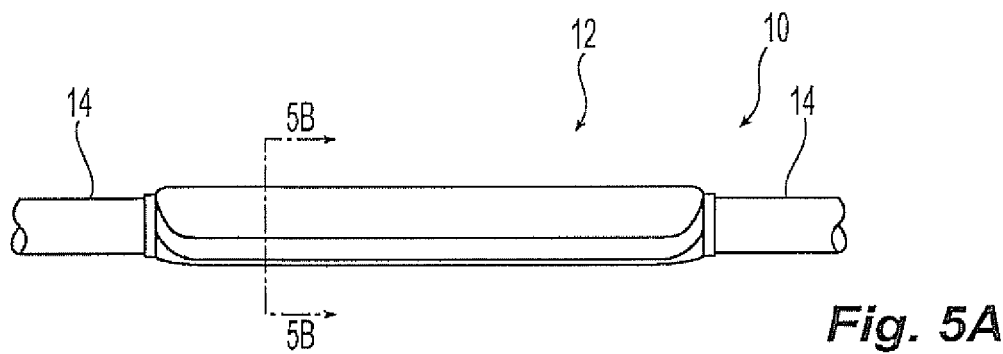
FIGS. 5A-5B are plan and cross-sectional views of a portion of a catheter and a deflated exemplary balloon.
Figure 5B:
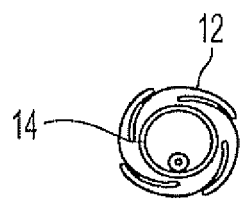
Figure 6A:
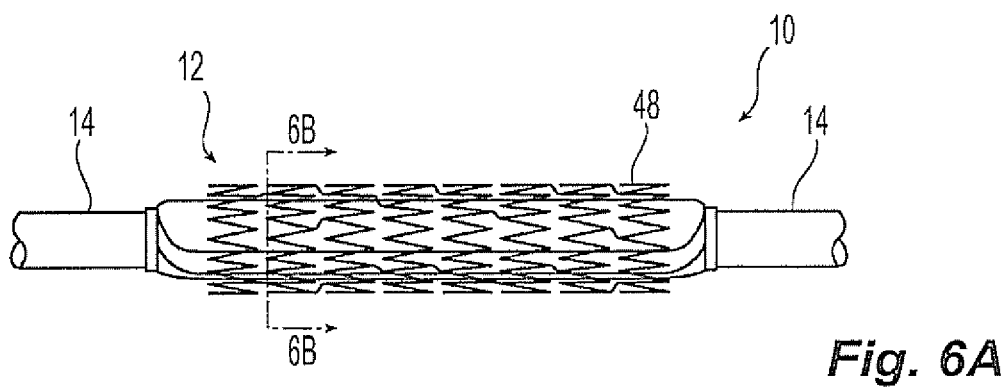
FIGS. 6A-6B are plan and cross-sectional views of the catheter and balloon of FIGS. 5A and 5B with an exemplary implantable device.
Figure 6B:
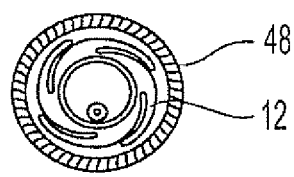

The deflated balloon 12 is preferably folded and wrapped circumferentially about itself to provide a reduced profile to the balloon 12. The wrapped balloon 12 preferably assumes a profile having an outer diameter that is similar to or approximately matching the outer diameter of the catheter tube 14. FIGS. 5A-5B illustrate an exemplary folded balloon. Referring to FIGS. 6A-6B, a portion of the exterior of the wrapped balloon 12 is formed to hold a medical device 48 in a collapsed state, which is preferably a stent that is compressed or collapsed to a delivery diameter. The inflation of the balloon 12 preferably applies an expanding force to the interior of the medical device 48 to cause it to expand to a greater diameter. After the medical device 48 has been expanded, and if designed to maintain a stable expanded configuration, the balloon 12 is preferably deflated and withdrawn from the interior of the medical device 48, thereby disengaging from the medical device 48.

Figure 7A:
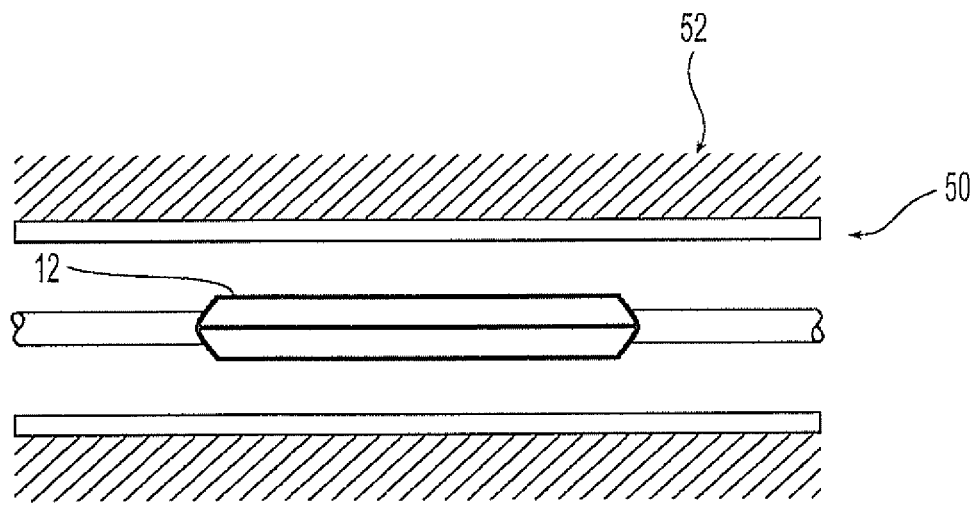
FIGS. 7A-7B are cross-sectional plan views of a deflated and inflated exemplary balloon, illustrating the radiopaque image provided by the balloon wall.
Figure 7B:
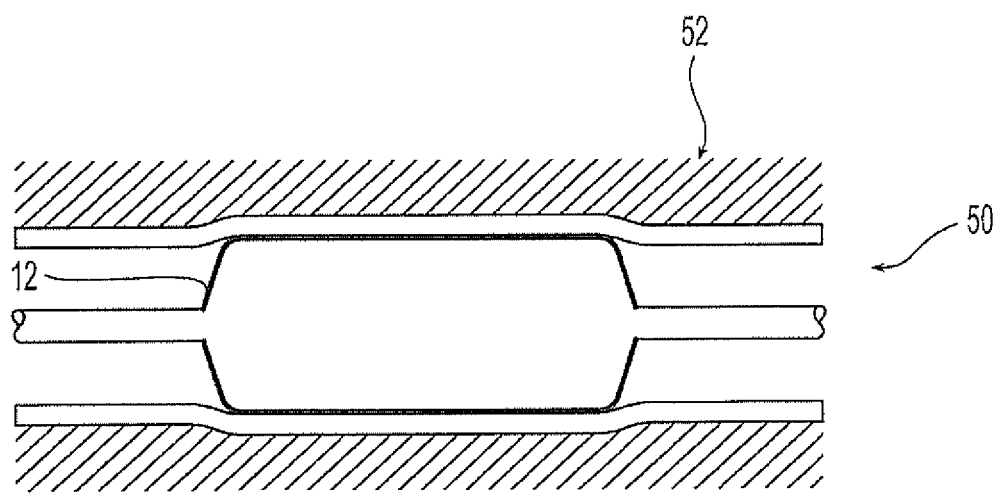

Referring to FIG. 7A, the deflated balloon 12 is preferably inserted into a vessel 52 and positioned relative to a region of interest 50. Referring to FIG. 7B, once positioned, the balloon 12 is preferably inflated to cause the exterior surface of the balloon to contact and press against the walls of the vessel 52 in the region of interest 50. The an alternative embodiment having a medical device 48 mounted on the deflated balloon 12, the inflation of the balloon 12 expands the medical device 48 to cause the exterior of the medical device to press against the vessel walls to achieve a therapeutic effect. The balloon 12 is preferably inflated with an inflation fluid delivered to the interior of the balloon through a lumen.

The quantity of radiopaque material 36 in the balloon wall 28 is fixed when the balloon wall is manufactured, which defines the total radiographic quantity for the balloon 12. Referring to FIGS. 7A and 7B, the constant quantity of radiopaque material in the balloon 12 provides a radiographic density that exhibits a relatively intense average radiopaque image (as compared to the radiopaque image of the inflated balloon) when the balloon is wholly or partially folded, deflated, empty, collapsed, and/or minimally filled with an inflation fluid, such as saline, because the radiopaque material 36 within the adhesive 34 of the balloon 12 will be closely packed together in the folded balloon 12. The deflated balloon 12 will also have a relatively greater radiopaque density as compared to the inflated balloon. The center portion of an image of the balloon 12 will also provide a radiographic image intensity that exhibits a relatively less pronounced radiopaque image when the balloon is fully inflated with inflation fluid because the radiopaque material 36 in the balloon wall 28 will have moved apart to a greater radial distance from the longitudinal axis of the catheter during the inflation process to cause a relative lighter radiopaque image. Also the edges of the balloon in an image of the balloon will maintain a comparatively intense image during and after inflation because the image of wall is obtained at an oblique angle in which the imaging radiation passes through or reflects off the wall in a direction that is nearly parallel to the surface of the wall, which causes the radiation to be affected by additional radiopaque material as compared to when the radiation passes through the wall at a right angle. The inflated balloon 12 as a whole will also have a relatively reduced radiographic image intensity as the balloon inflates because of the increase in balloon volume resulting from the inflation of the balloon. The balloon 12 as a whole will also provide a varying radiopaque image as the balloon 12 progresses between the radiopaque extremes provided in the deflated and inflated states of the balloon 12, with a more intense radiopaque image provided with the deflated balloon and a less intense radiopaque image provided with the inflated balloon. Furthermore, the center of the image of the balloon will exhibit a relatively intense image when deflated and a relatively less intense image when inflated, and the edges of the image of the balloon will exhibit a relatively constant radiopaque image.

The balloon 12 thus has an radiographic density that changes when the balloon 12 transitions between deflated and inflated states, which directly corresponds to volume of the balloon at any point relative to the fixed quantity of radiopaque material 36 in the balloon wall 28. Specifically, the image of the center of the radiopaque balloon 12 becomes radiographically lighter as the balloon is inflated, whereas conventional balloons that are not radiopaque become radiographically darker at the center of the balloon image because of the presence of a radiopaque inflation fluid.

The radiographic density of the entire balloon 12 is determined by comparing the fixed quantity of radiopaque material 36 to the entire volume of the balloon 12. As the total quantity of radiopaque material in the balloon wall 28 is constant, changes in balloon volume cause the radiographic density to change. Referring to FIG. 7A, the radiographic density of the folded balloon 12 is relatively high because the fixed volume of radiopaque material 36 is contained in a relatively small volume of the folded balloon 12. Referring to FIG. 7B, the radiographic density of the inflated balloon 12 is relatively low because the fixed volume of radiopaque material 36 is contained in relatively large volume of the inflated balloon 12. The average change in radiographic density between a fully-deflated, folded balloon and a fully-inflated balloon is proportional to the change in the diameters of the balloon in these two conditions.

It is believed that, during a typical medical procedure, the balloon is typically imaged on a fluoroscope from a position perpendicular to the main balloon axis. From this perspective, the distribution of radiopaque material in the balloon wall provides an image that is advantageously not uniform. The radiopaque balloon 12 provides an image that appears to be more radiopaque material at and very near the edges of the balloon image, and less in the center region of the balloon. As such, the image intensity of the center region of the balloon is diminished even further when the balloon is inflated. Table 1 below shows the change in average radiographic density for various size balloons of a typical construction, as well as the change that occurs in the center region of the balloon.

TABLE 1

Change in radiographic image intensity resulting from inflation for various balloon sizes

| Inflated balloon outer diameter (mm) | Deflated balloon outer diameter (mm) | Decrease in total balloon radiographic image intensity when balloon is inflated from deflated state (%) | Decrease in balloon radiographic image intensity in center region of balloon image when balloon is inflated from deflated state (%) |
|---|---|---|---|
| 5 | 2.03 | 59.4 | 71.3 |
| 6 | 2.03 | 66.2 | 76.1 |
| 7 | 2.03 | 71.0 | 79.5 |
| 8 | 2.03 | 74.6 | 82.1 |
| 9 | 2.23 | 75.2 | 82.5 |
| 10 | 2.23 | 77.7 | 84.2 |
| 12 | 2.41 | 79.9 | 85.8 |
| 14 | 2.33 | 83.4 | 88.2 |
| 16 | 2.64 | 83.5 | 88.3 |
| 18 | 2.69 | 85.1 | 89.4 |
| 20 | 2.95 | 85.3 | 89.6 |
| 22 | 3.3 | 85.0 | 89.4 |
| 24 | 3.99 | 83.4 | 88.2 |
| 26 | 3.99 | 84.7 | 89.1 |

The decrease in total radiographic image intensity between the fully-deflated and fully-inflated balloon preferably ranges from 35-95%, and more preferably ranges from 60-90%.

The distribution of radiopaque adhesive in the balloon, as viewed under a fluoroscope, is an important feature of this invention, as compared to a non-radiopaque balloon filled with radiopaque contrast media. FIGS. 8 and 9 illustrate this effect. Since the x-rays used for imaging pass through the balloon in a direction roughly perpendicular to the longitudinal axis of the balloon, the amount of radiopaque adhesive that the x-ray beam encounters is significantly greater at and very near the edges of the balloon, as compared to other areas of the balloon image disposed within the edges of the balloon image. This greater interaction with x-rays at the edges of the balloon image yields an image of a balloon that has defined edges in the image. The increase in radiographic density at the balloon image edge, compared to the balloon image center, is a function of the diameter of the inflated balloon and the thickness of the radiopaque adhesive layer. Table 2 shows the difference in radiographic image intensity presented by the edges of the imaged balloon as compared to the center of the imaged balloon, for several balloon sizes and radiopaque adhesive thicknesses. Increases in radiographic image intensity at the imaged balloon edge range from 560% to over 2000% as compared to the imaged balloon center.

TABLE 2

Radiographic image intensity comparison between balloon image edge and balloon image center

| Balloon size (mm) | Radiopaque adhesive thickness (mm) | Thickness of radiopaque adhesive encountered by x-rays directed at the imaged balloon edge from a position orthogonal to the balloon axis (mm) | Difference between image intensity at balloon image edge compared to imaged balloon center (%) |
|---|---|---|---|
| 5 | 0.025 | 0.5006 | 1001 |
| 6 | 0.025 | 0.5483 | 1097 |
| 7 | 0.025 | 0.5921 | 1184 |
| 8 | 0.025 | 0.6329 | 1266 |
| 9 | 0.025 | 0.6713 | 1343 |
| 10 | 0.025 | 0.7075 | 1415 |
| 12 | 0.025 | 0.7750 | 1550 |
| 14 | 0.025 | 0.8370 | 1674 |
| 16 | 0.025 | 0.8948 | 1790 |
| 18 | 0.025 | 0.9490 | 1898 |
| 20 | 0.025 | 1.0003 | 2001 |
| 22 | 0.025 | 1.0491 | 2098 |
| 24 | 0.025 | 1.0957 | 2191 |
| 26 | 0.025 | 1.1404 | 2281 |
| 5 | 0.075 | 0.8693 | 580 |
| 6 | 0.075 | 0.9516 | 634 |
| 7 | 0.075 | 1.0274 | 685 |
| 8 | 0.075 | 1.0980 | 732 |
| 9 | 0.075 | 1.1643 | 776 |
| 10 | 0.075 | 1.2270 | 818 |
| 12 | 0.075 | 1.3437 | 896 |
| 14 | 0.075 | 1.4511 | 967 |
| 16 | 0.075 | 1.5510 | 1034 |
| 18 | 0.075 | 1.6449 | 1097 |
| 20 | 0.075 | 1.7337 | 1156 |
| 22 | 0.075 | 1.8181 | 1212 |
| 24 | 0.075 | 1.8988 | 1266 |
| 26 | 0.075 | 1.9763 | 1318 |

Figure 8A:
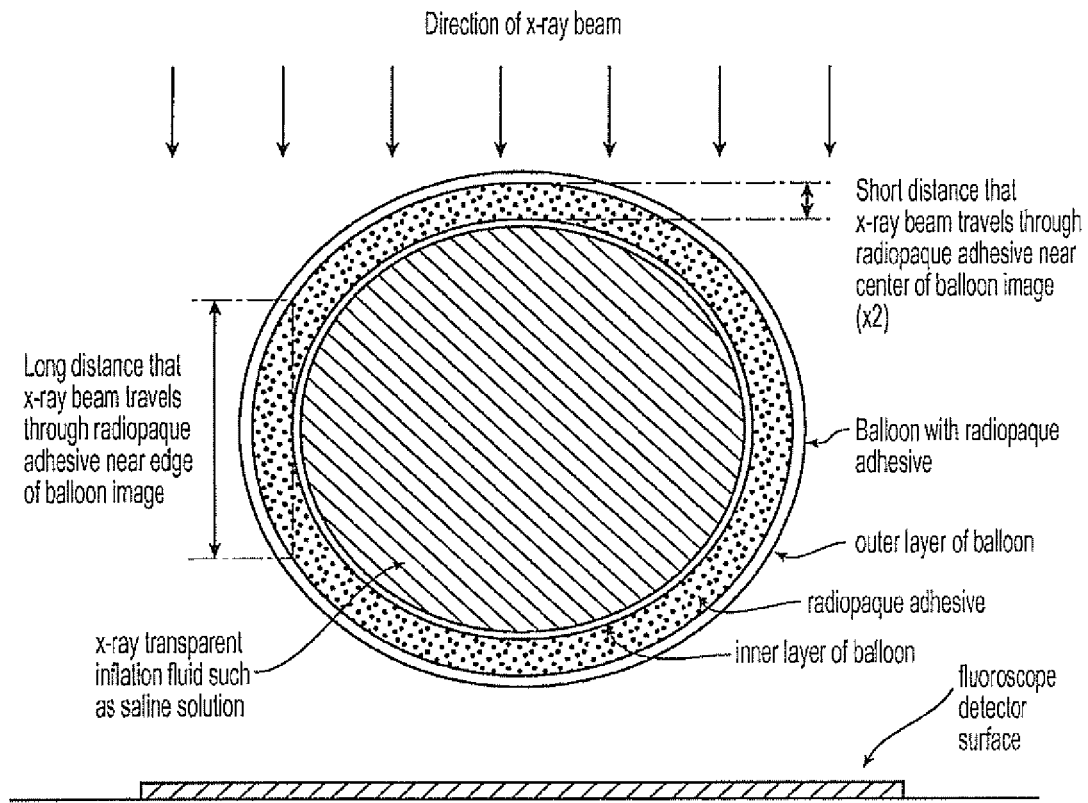
FIG. 8A illustrates x-ray imaging directed at the side of a balloon with a radiopaque adhesive and FIG. 8B represents the image intensity provided by the x-ray imaging.
Figure 8B:
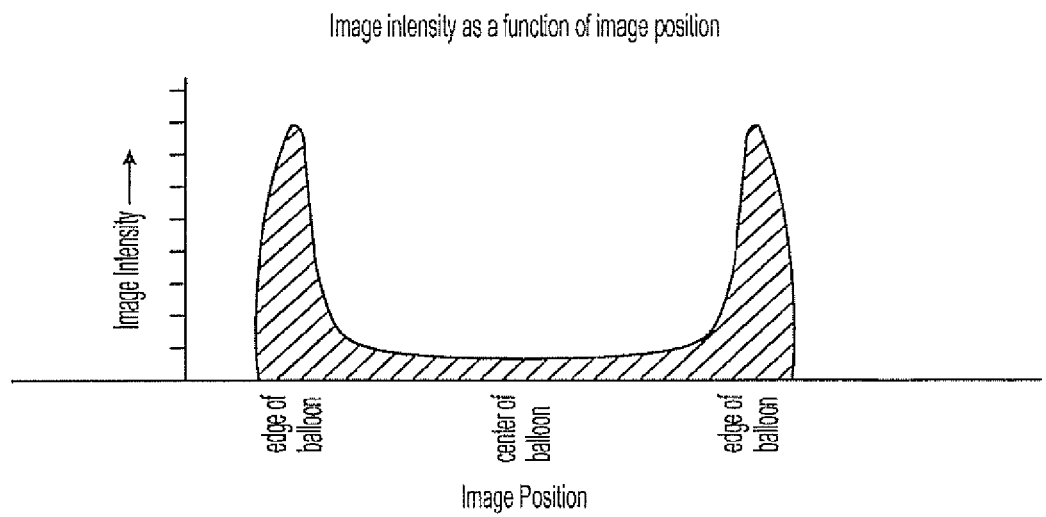
Figure 9A:
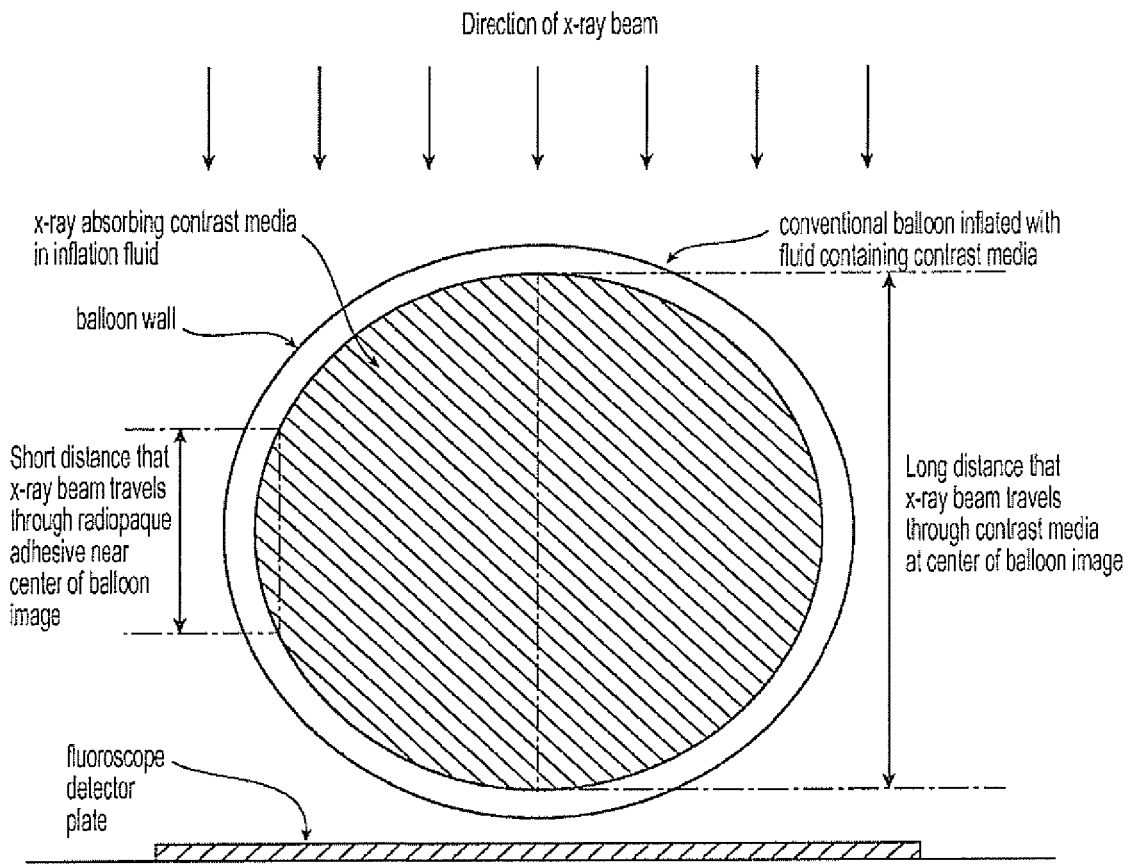
FIG. 9A illustrates x-ray imaging directed at the side of a conventional balloon filled with a radiopaque contrast media and FIG. 9B represents the image intensity provided by the x-ray imaging.
Figure 9B:
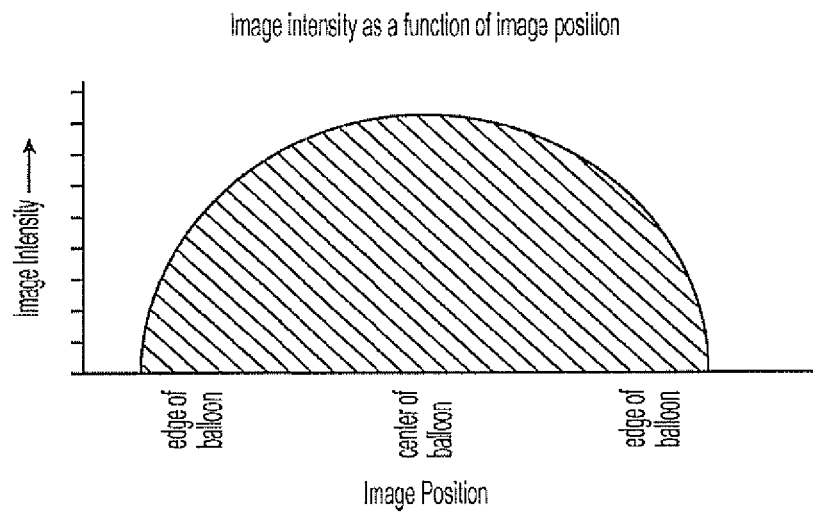

The intensity of the imaged balloon edge of a balloon with a radiopaque adhesive is comparable to the intensity of the imaged balloon edge produced by a conventional non-radiopaque balloon that is filled with a radiopaque contrast media. FIGS. 8A-9B illustrate the distribution of radiographic image intensity that is observed in this comparison. As illustrated in FIG. 8A, illustrating x-rays directed at the side of a balloon with a radiopaque adhesive, and FIG. 8B, representing the image intensity provided by the x-ray imaging, the balloon image intensity is most intense at the imaged edges of the balloon. In comparison, FIG. 9A, illustrating x-rays directed at the side of a conventional balloon filled with a radiopaque contrast media, and FIG. 9B, representing the image intensity provided by the x-ray imaging, the balloon image intensity is nonexistent at the edges of the balloon and minimally intense adjacent to the imaged edges of the form presented by the contrast media. Conventional balloons using contrast media are thus believed to provide a fuzzy and poorly defined imaged balloon edge because the x-rays do not image the balloon itself, and because the contrast media imaged near the edges of the form outlined by the contrast media has a minimal or negligible thickness as compared to the thickness presented at the center of the imaged balloon.

Referring to FIGS. 7A and 7B, the balloon wall 28 itself (disregarding any inflation fluid or the volume of the balloon) has an constant balloon wall radiographic density that does not change relative to the inflation state of the balloon 12, and that provides an image of the balloon 12 in all inflation states. When the deflated balloon 12 is folded, the balloon wall 28 exhibits the same total radiopacity as when the balloon is inflated because the density of the radiopaque material 36 in the balloon wall 28 has not changed. The radiopaque image presented of the folded balloon wall 28, as illustrated in FIG. 7A, is the additive radiopacities of the folded portions of the balloon wall 28, and the total radiopacity of the folded balloon is thus a function or factor of the radiopacity contribution of each fold of the balloon wall.

The inflation of the balloon 12 is preferably achieved by supplying the inflation fluid to the interior of the balloon 12 via the catheter tube 14. The inflation fluid is preferably a mixture of a physiological saline solution and a radiopaque contrast media, or pure physiological saline solution. Available contrast media include iodinated compounds that are either monomeric or dimeric in structure, which includes acetrizoate (Diaginol, Urokon), diatrizoate (Angiographin, Renografin, Urovison), iodamide (Uromiro), ioglicate (Rayvist), iothalamate (Conray), ioxithalamate (Telebrix), iotrolan (Isovist), iodixanol (Visipaque), iohexol (Omnipaque), iopentol (Imagopaque) and ioversol (Optiray). Another type of contrast media includes chelates of rare earth or other heavy metal species, such as gadolinium, holmium, manganese or dysprosium provided in commercially-available products such as Dotarem, Omniscan, Eovist, Prohance, and Multihance products. The inflation fluid is preferably prepared to have a concentration of radiopaque fluid that is less than 50%. The inflation fluid more preferably has a concentration of radiopaque fluid that is from 0% (pure saline solution) to approximately 40%, and yet more preferably in range of approximately 0-20%, and still more preferably in a range of approximately 0-5%, and most preferably at a concentration of 0%.

Generally, it is believed that radiopaque fluids have a viscosity that is greater than the viscosity of pure physiological saline. Likewise, it is believed that mixtures of saline with radiopaque fluids have viscosities that are less than undiluted radiopaque fluid but still greater than the viscosity of pure saline. It is also believed that the greater viscosities of radiopaque fluids and saline/radiopaque fluid mixtures cause such fluids to move, at a given pressure, more slowly through tubing than the movement observed with pure saline under the same conditions. The greater viscosities of radiopaque fluids, compared to pure saline, thus require greater head pressures to push the radiopaque fluids through tubing, and greater head pressures to achieve the balloon inflation times achieved with saline under the same conditions. The relatively higher viscosities of radiopaque fluids thus cause the balloon 12 to fill more slowly as compared to a balloon inflated with pure saline. This effect becomes even more pronounced with balloon deflation. This is because, unlike inflation, it is not possible to apply a high pressure on the fluid in the balloon to force it to flow out of the catheter during deflation. The maximum pressure available for forcing fluid out is limited to a vacuum that depends in the ambient atmospheric pressure available (14.7 psi or 1 atmosphere). Deflation of the balloon can thus take a considerable time depending on the catheter construction and balloon size. All of these factors are believed to increase the time and/or effort required to complete a medical procedure involving the use of a conventional balloon and radiopaque imaging, and an increase in the time required to achieve balloon inflation or deflation.

The relation of inflation fluid density (concentration of radiopaque fluid in saline) to balloon deflation time is illustrated in Table 3.

TABLE 3

Relation of inflation fluid density and balloon deflation time

| Concentration of radiopaque fluid in saline (%) | Mean deflation time of fully-inflated balloon (seconds) |
|---|---|
| 0% | 6.20 |
| 25% | 8.18 |
| 50% | 11.45 |
| 75% | 18.30 |
| 100% | 53.29 |

Accordingly, the exemplary radiopaque balloon provides advantages over existing balloons that do not have a radiopaque balloon wall. The exemplary balloon provides faster inflation and deflation times because the balloon produces an image with an imaging system while being inflated with a less viscous fluid as used with convention balloons. Also, the exemplary balloon provides a balloon that uses less or no radiopaque fluid, and thus provides a simpler and less expensive method for inflating and imaging a balloon. When the inflation solution is pure saline solution, the time and expense of mixing solutions is eliminated entirely from the balloon inflation and deflation process.

The reduced deflation time, and ease with which the balloon can be deflated, with a balloon containing a radiopaque adhesive in the balloon wall, also avoids a potentially serious complication that can occur during a medical procedure. It is believed that viscous fluids containing contrast media are more likely to permit a balloon to appear to deflate but leave a significant quantity of media in the apparently-deflated balloon. When the catheter is subsequently moved to initiate extraction of the catheter from the patient, by repositioning the apparently-deflated balloon in an introducer tube, the media remaining in the apparently-deflated balloon can be forced towards the distal end of the balloon to inflated the distal-most end of the balloon that resists complete withdrawal of the balloon into the introducer tube. This condition is further exasperated because an inflation/deflation eyehole permitting the further deflation of the balloon can be pinched shut by the pressure exerted on the balloon by the constructing introducer tube as it presses against the bolus of media trapped in the balloon. As can be appreciated, the results of such a situation could create an adverse health risk for the patient, rupture the balloon and release media, and increase the length and complexity of the medical procedure.

Additional examples of a balloon with a radiopaque adhesive in a balloon wall are provided below.

EXAMPLE 1

A radiopaque adhesive was prepared by adding the following components into a glass mixing vessel:
1) 54 grams of a polyurethane laminating adhesive available as Tecoflex® 1-MP adhesive having approximately 8.5 wt. % polyurethane in solvent;
2) 24.5 grams of tungsten powder, 0.5 micron nominal particle size; and
3) 36.6 grams of methyl ethyl ketone (MEK).
The components were mixed to produce an adhesive with a homogeneous composition of approximately 25 wt % solids.

Polyethylene terephthalate (PET) angioplasty balloons, measuring 12 mm in diameter and with a double wall thickness of approximately 0.002 of an inch, were mounted on mandrels to allow the balloons to be inflated. The inflated balloons were sprayed with the radiopaque adhesive to dispose a uniform quantity of adhesive over the surface of the balloons. The adhesive was rapidly dried on the surface of the balloon. The dried adhesive contained approximately 26 volume % of tungsten and 74 volume % polyurethane.

The balloons were then wrapped helically with a thin strip of polyether-polyamide copolymer film commercially available as Pebax®. The film thickness, of approximately 0.0005 of an inch, was stretched during wrapping to further reduce the thickness. Once wrapped, the balloons were placed in laminating dies of a size and shape to allow heat and pressure to be applied to the balloon surface. Balloons were heated to a temperature of approximately 220 degrees F. with pressure applied to the surface of the balloon to cause the radiopaque laminating adhesive to flow and consolidate the balloon and Pebax® film.

The result was a radiopaque angioplasty balloon with a double wall thickness of 0.0045 of an inch. The balloons were examined by x-ray imaging and showed excellent visibility without the need to fill them with contrast media. A control of conventional PET balloons of the same size did not exhibit a visible image under the same x-ray imaging.

EXAMPLE 2

A radiopaque laminating adhesive was prepared by adding the following components into a glass mixing container:
1) 61 grams of a polyurethane laminating adhesive available as Tecoflex® 1-MP adhesive;
2) 14.6 grams of bismuth trioxide powder;
3) 24.4 grams of MEK; and
4) 15 grams of acetone.

The components were mixed to produce an adhesive with a homogeneous composition of approximately 17 wt % solids.

Polyethylene terephthalate (PET) angioplasty balloons, measuring 12 mm in diameter and with a double wall thickness of approximately 0.002 of an inch, were mounted and sprayed with the adhesive and dried as described in Example 1. The dried adhesive contained approximately 26 volume % of bismuth trioxide, and 74 volume % polyurethane. The balloons were then wrapped helically with Pebax® film and laminated under heat and pressure as described in Example 1 to produce consolidated laminated balloons.

The result was a radiopaque angioplasty balloon with a double wall thickness of 0.0046 of an inch. The balloons were examined by x-ray imaging and showed excellent visibility without the need to fill them with contrast media.

EXAMPLE 3

A radiopaque laminating adhesive was prepared by adding the following components into a plastic mixing container:
1) 297 grams of a polyurethane laminating adhesive available as Tecoflex® 1-MP adhesive;
2) 146 grams of bismuth trioxide powder;
3) 119 grams of MEK; and
4) 238 grams of acetone.

The components were mixed together briefly and then charged in a laboratory ball mill jar charged with aluminum oxide ceramic balls. The jar was then rolled on a ball mill roller for 24 hours to reduce the particle size of the bismuth trioxide, after which the mixture was removed from the ball mill and stored in a glass container. The result was an adhesive with a homogeneous composition of approximately 18 wt % solids.

Polyethylene terephthalate (PET) angioplasty balloons, measuring 12 mm in diameter and with a double wall thickness of approximately 0.002 of an inch, were mounted and sprayed with a thin coat of the adhesive and dried as described in Example 1. The dried adhesive contained approximately 43 volume % of bismuth trioxide and 57 volume % polyurethane. The balloons were then wrapped helically with Pebax® film and laminated under heat and pressure as described in Example 1 to produce consolidated laminated balloons.

The result was a radiopaque angioplasty balloon with a double wall thickness of 0.0065 of an inch. The balloons were examined by x-ray imaging and showed excellent visibility without the need to fill them with contrast media. Because of the higher concentration of bismuth trioxide in the laminating adhesive, and also because of the thicker layer of adhesive, the image for these balloons was more intense than for the balloons prepared in Example 2.

EXAMPLE 4

A radiopaque laminating adhesive was prepared by adding the following components into a glass mixing container:
1) 78 grams of a polyurethane laminating adhesive available as Tecoflex® 1-MP adhesive;
2) 78.2 grams of tungsten powder, submicron particle size;
3) 31.3 grams of MEK; and
4) 62.5 grams of acetone.

The components were mixed thoroughly to produce an adhesive having a homogeneous composition of approximately 25.4 wt % solids.

Polyethylene terephthalate (PET) angioplasty balloons, measuring 12 mm in diameter and with a double wall thickness of approximately 0.002 of an inch, were mounted and sprayed with the adhesive and dried as described in Example 1. The dried adhesive contained approximately 42 volume % of tungsten and 58 volume % polyurethane. The balloons were then wrapped helically with Pebax® film and laminated under heat and pressure as described in Example 1 to produce consolidated laminated balloons.

The result was a radiopaque angioplasty balloon with a double wall thickness of 0.006 of an inch. The balloons were examined by x-ray imaging and showed excellent visibility without the need to fill them with contrast media. Because of the higher concentration of tungsten in the laminating adhesive and also because of the thicker layer of adhesive as compared to Example 1, the image for the balloons was more intense than for the balloons prepared in Example 1.

EXAMPLE 5

A radiopaque laminating adhesive was prepared by adding the following components into a plastic mixing container:
1) 308 grams of a polyurethane laminating adhesive available as Tecoflex® 1-MP adhesive;
2) 123 grams of cerium oxide powder, 5 micron nominal particle size;
3) 123 grams of MEK; and
4) 246 grams of acetone.

The components were mixed together briefly and then charged into a laboratory ball mill jar charged with aluminum oxide ceramic balls. The jar was then rolled on a ball mill roller for 24 hours to reduce the particle size of the cerium oxide, after which the mixture was removed from the ball mill and stored in a glass container. The result was an adhesive with a homogeneous composition of approximately 19 wt % solids.

Polyethylene terephthalate (PET) angioplasty balloons, measuring 12 mm in diameter and with a double wall thickness of approximately 0.002 of an inch, were mounted and sprayed with the adhesive and dried as described in Example 1. The dried adhesive contained approximately 43 volume % of cerium oxide and 57 volume % polyurethane. The balloons were then wrapped helically with Pebax® film and laminated under heat and pressure as described in Example 1 to produce consolidated laminated balloons.

The result was a radiopaque angioplasty balloon with a double wall thickness of approximately 0.0062 of an inch. The balloons were examined by x-ray imaging and showed excellent visibility without the need to fill them with contrast media.

EXAMPLE 6

A radiopaque laminating adhesive was prepared as described in Example 5. Polyethylene terephtalate (PET) angioplasty balloons, measuring 12 mm in diameter and with a double wall thickness of approximately 0.002 of an inch, were mounted and sprayed with a small amount of the adhesive and allowed to dry. The layer of adhesive was then wrapped circumferentially with a 50 denier yarn composed of ultrahigh molecular weight polyethylene (UHMWPE) commercially available as Spectra® yarn. The yarn was applied at a pitch of approximately 50 threads per inch to wrap the balloon. The wrapped balloon was then sprayed with additional radiopaque adhesive sufficient to fill in around the fibers and to cover them. The balloons were then wrapped helically with Pebax® film and laminated under heat and pressure as described in Example 1 to produce consolidated laminated fiber-reinforced balloons.

The result was a fiber-reinforced radiopaque angioplasty balloon with a double wall thickness of approximately 0.0064 of an inch. The balloons were examined by x-ray imaging and showed excellent visibility without the need to fill them with contrast media.

EXAMPLE 7

A radiopaque laminating adhesive was prepared by adding the following components into a plastic mixing container:
1) 278 grams of a polyurethane laminating adhesive available as Tecoflex® 1-MP adhesive;
2) 89 grams of cerium oxide powder, 5 micron nominal particle size;
3) 112 grams of MEK;
4) 223 grams of acetone; and
5) 0.22 grams of a phthalocyanine green pigment.

The components were mixed together briefly and then charged into a laboratory ball mill jar charged with aluminum oxide ceramic balls. The jar was then rolled on a ball mill roller for 24 hours to reduce the particle size of the cerium oxide, after which the mixture was removed from the ball mill and stored in a glass container. The result was an adhesive with a homogeneous light green colored composition of approximately 16 wt % solids.

Polyethylene terephthalate (PET) angioplasty balloons, measuring 12 mm in diameter and with a double wall thickness of approximately 0.002 of an inch, were mounted and sprayed with a thin layer of the adhesive and dried as described in Example 1. The dried adhesive contained approximately 38 volume % of cerium oxide and 62 volume % polyurethane. A 50-denier Spectra® yarn was then wrapped circumferentially about the balloon as described in Example 6. The green color of the adhesive layer facilitated the visualization of the fibers during the wrapping process. Additional radiopaque adhesive was then applied sufficient to fill in around the fibers and to cover them. The balloons were then wrapped helically with Pebax® film and laminated under heat and pressure as described in Example 1 to produce consolidated laminated balloons.

The result was a radiopaque angioplasty balloon with a double wall thickness of approximately 0.0057 of an inch. The balloons were examined by x-ray imaging and showed excellent visibility without the need to fill them with contrast media.

While the present invention has been disclosed with reference to certain embodiments, numerous modifications, alterations, and changes to the described embodiments are possible without departing from the sphere and scope of the present invention, as defined in the appended claims. For example, the ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Accordingly, it is intended that the present invention not be limited to the described embodiments, but that it has the full scope defined by the language of the following claims, and equivalents thereof.

What is claimed is:
1. A balloon, comprising:
a first balloon wall layer disposed about a longitudinal balloon axis;
a second balloon wall layer disposed on an exterior of the first balloon wall layer;
an adhesive including a radiopaque material dispersed within an adhesive base, said adhesive disposed between the first balloon wall layer and the second balloon wall layer, the adhesive having a first radiopacity, the adhesive adhering the first balloon wall layer to the second balloon wall layer; and
a layer of marker material forming at least one radiopaque marker, said radiopaque marker having a second radiopacity different from the first radiopacity.
2. The balloon of claim 1, the adhesive disposed along an entire length or circumference of the balloon.
3. The balloon of claim 1, wherein the first or second balloon wall layer comprises a fiber layer.
4. A balloon, comprising: a balloon wall having first and second balloon wall layers and a radiopaque-infused adhesive disposed between the first and second balloon wall layers, the adhesive forming a layer adhering the first balloon wall layer to the second balloon wall layer and providing a constant radiographic density, the balloon having a deflated radiographic density of the balloon and a lesser inflated radiographic density of the balloon, wherein the inflated radiographic density of the balloon provides an image intensity that is 35% to 95% of an image intensity provided by the deflated radiographic density of a fully deflated balloon.

5. The balloon of claim 4, the deflated and inflated radiographic densities defined by a radiopacity value of the entire balloon related to a total volume value of the balloon.

6. The balloon of claim 5, the radiopacity value of the entire balloon remaining constant between inflated and deflated states of the balloon.

7. The balloon of claim 1, wherein the adhesive comprises an intrinsically radiopaque polymeric material.

8. The balloon of claim 7, wherein the intrinsically radiopaque polymeric material contains heteroatoms covalently or ionically bonded into a polymer structure.

9. The balloon of claim 1, wherein the adhesive is provided at first and second spaced locations on a radially exterior surface of the first balloon wall layer.

10. The balloon of claim 1, wherein the adhesive comprises a first adhesive having a first radiopaque property that provides a first radiopaque image and a second adhesive having a second radiopaque property that provides a second radiopaque image that is less intense than the first radiopaque image.

11. The balloon of claim 1, wherein the adhesive provides a radiopaque image, and further including a second adhesive that does not provide a radiopaque image.

12. The balloon of claim 1, further including a device mounted on the balloon, wherein a radiopacity of the deflated balloon is greater than a radiopacity of the device mounted on the balloon.

\* \* \* \* \*